M. Mattson.

Breast Pump.

No. 4,282. Reissued Feb. 28. 1871.

Witnesses.

A. Gurlitz.

C. F. Brooksaw

Inventor.

M. Mattson by his atty.

L. D. Lam

N. PETERS, PHOTO-LITHOGRAPHER, WASHINGTON, D. C.

United States Patent Office.

MORRIS MATTSON, OF NEW YORK, N. Y.

Letters Patent No. 85,318, dated December 29, 1868; reissue No. 4,282, dated February 28, 1871.

IMPROVEMENT IN BREAST-PUMPS.

The Schedule referred to in these Letters Patent and making part of the same.

*To all whom it may concern:*

Be it known that I, MORRIS MATTSON, of the city of New York, in the county of New York and State of New York, have invented a new and useful Improvement in Breast-Pumps; and I do hereby declare that the following is a full, clear, and exact description thereof, and of its mode or manner of operation, reference being had to the accompanying drawing and to the letters of reference marked thereon and making a part of this specification.

My present invention is for a construction of breast-pump resembling that patented to me on the 8th day of September, 1868, but differing therefrom in some particulars, which renders it better adapted for use under certain circumstances.

The breast-pump patented to me September 8, 1868, consists of two principal parts: a vacuum-glass, with a trumpet-shaped mouth, so formed as to prevent any essential compression of the milk-ducts when the exhaustion is produced, for the purpose of drawing the milk, and an elastic exhausting-bulb having double valves, *i. e.*, an inlet and an outlet-valve.

At the time of obtaining such patent it was considered that a bulb, to be most efficient, should have a double set of valves; but subsequent experiments have shown that, for some uses, or for use under certain conditions of the female breast, a breast-pump with an exhausting-bulb having but a single valve is preferable.

In the use of an elastic bulb having double valves, such valves are arranged at opposite ends of the bulb, and in compressing the bulb the inlet-valve closes, and does not permit any portion of the air within the bulb, undergoing compression, to pass into the vacuum-glass or cup.

The single valve *a'*, however, which is arranged at the upper end of the bulb A, as an outlet-valve, has a different action.

When the bulb is compressed, the air which it contains does not entirely escape through the outlet-valve *a'*, but a portion of it is forced back into the vacuum-glass B, and cannot be wholly expelled without further compression and expansion of the bulb.

Figure 2:
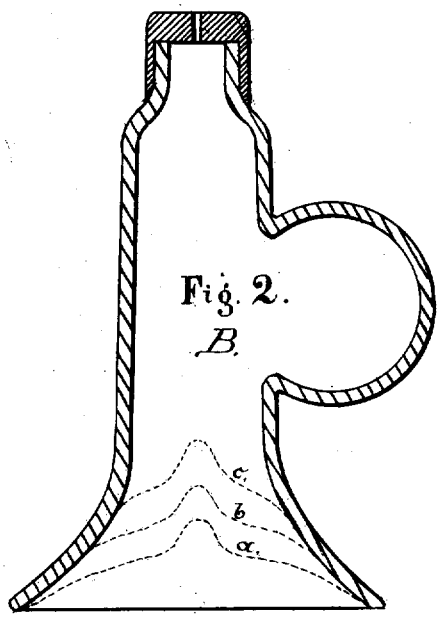
Figure 2 is a vertical section of the vacuum-glass, and showing also the different positions of the breast as it rises in the glass.

A reference to fig. 2, and the dotted wave lines *a b c* therein, showing different positions of the nipple and breast, will show more clearly how the use of a single valve produces a different result from the use of the double valves.

If the vacuum-glass B, in proper working order, be placed in contact with the breast, in the usual manner, so that there shall be no leakage of air, and the bulb, fitted with double valves, be slightly compressed and then allowed to expand, the breast will ascend to the wave-line *a*, and there remain stationary.

If the bulb be slightly compressed a second time, and then allowed to expand, the nipple and breast, without receding from *a*, will ascend toward or to the second line *b*, and, in the same manner, will ascend toward or to the wave-line *c*, from similar compression or expansion of the bulb.

Figure 3:
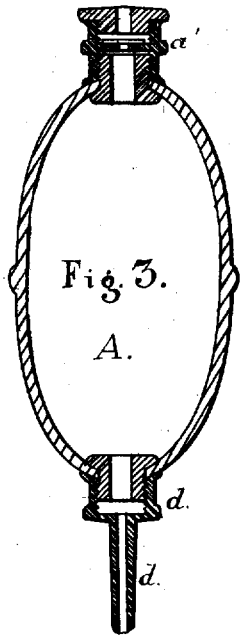
Figure 3 is a sectional view of the exhausting-bulb.

If a bulb with a single valve, like that represented in section in fig. 3, be used in connection with the vacuum-glass B, instead of a bulb with double valves, and such bulb be compressed at intervals, as before mentioned, the breast will ascend to the wave or dotted lines *a b c*, but with the following difference in action or operation: that, at the moment the bulb is compressed, the nipple and breast will first descend a little below its line, and then ascend to a higher line at the instant the bulb undergoes expansion.

This action is due to a portion of the air being forced into the vacuum-glass by the compression of the bulb, there being no valve to prevent it; and the pressure of the air thus produced is sufficient to cause the breast to recede, as already described. This action, or the depressing and rising of the nipple and breast, is repeated at every compression and expansion of the bulb.

Thus we have what may be termed vibratory movements of the breast, and such movements may be rapid or slow, in proportion as the bulb is rapidly or slowly operated.

These vibratory movements are closely analogous to the movements produced by the nursing of the infant, and are, therefore, the closest possible imitation of nature.

In a breast in which the milk flows freely, there seems to be no choice between the bulb having single or double valves; but at the commencement of lying-in, or at other periods when the milk-ducts are more or less obstructed, or the milk itself in a thick or creamy condition, so that its flow is tardy or difficult, the single-valved bulb is greatly preferable, because the vibratory movements resulting from its use aid essentially in procuring a gentle and painless flow of the milk.

Such vibratory movements of the breast resulting, from the use of a single-valved bulb, are also useful in other vacuum instruments besides the breast-pump; for instance, serving to establish a better circulation in blood-vessels which are torpid or inactive.

Figure 1:
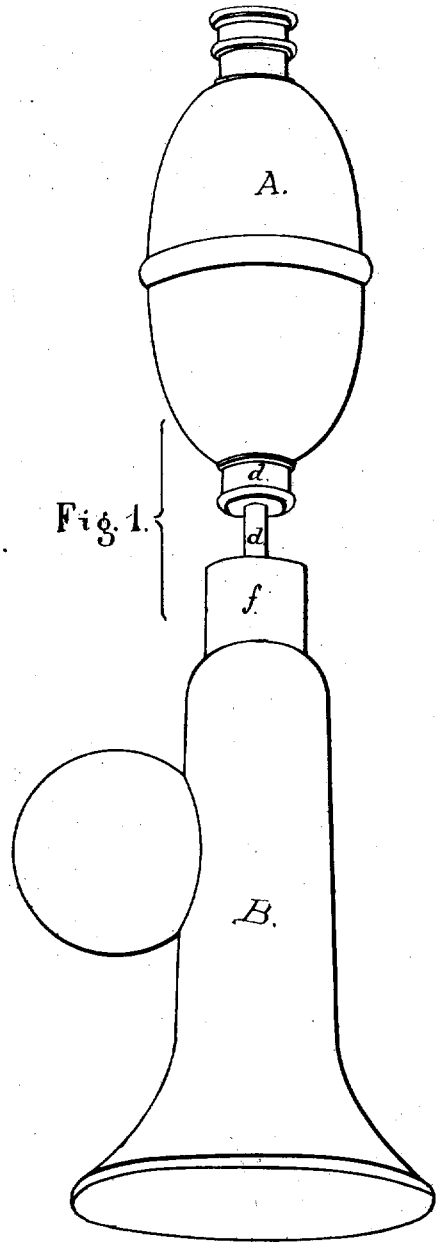
Figure 1 is a general perspective view of my improved instrument complete.

Instead of a bulb with a metallic nose and pipe *d d* to connect, as shown, with the vacuum-glass by means of a rubber cup, *f*, as shown in fig. 1, the bulb may have a tubular neck to couple directly with the vacuum-glass.

Any kind of suitable working valve may be used in connection with the bulb; but I prefer the loose floating valve patented to me April 4, 1854, extended March 30, 1868.

What I claim as my invention, and desire to secure by Letters Patent, is—

The combination, with a vacuum-glass, of an elastic exhausting bulb, A, having or employing a single valve or valvular apparatus located at the end of the bulb furthest from the vacuum-glass, substantially as and for the purposes set forth.

M. MATTSON.

Witnesses:
S. D. LAW,
A. T. GURLITZ.